United States Patent [19]

Taboada

[11] Patent Number: 5,521,386

[45] Date of Patent: May 28, 1996

[54] GAMMA RAY CAMERA METHOD AND APPARATUS

[75] Inventor: John Taboada, San Antonio, Tex.

[73] Assignee: The United States of America as represented by the Secretary of the Air Force, Washington, D.C.

[21] Appl. No.: 387,002

[22] Filed: Feb. 9, 1995

[51] Int. Cl.[6] .............................. G01T 1/161; G01T 1/20
[52] U.S. Cl. .............. 250/363.02; 250/368; 250/214 VT
[58] Field of Search .............................. 250/363.02, 368, 250/214 VT, 363.10, 370.11

[56] References Cited

U.S. PATENT DOCUMENTS

| | | |
|---|---|---|
| 2,776,377 | 1/1957 | Anger . |
| 2,779,876 | 1/1957 | Tobias et al. . |
| 3,749,920 | 7/1973 | Sheldon ........................... 250/214 VT |
| 3,774,031 | 11/1973 | Mallard et al. ............. 250/214 VT X |
| 4,438,334 | 3/1984 | Jatteau et al. ....................... 250/363.02 |
| 4,672,207 | 6/1987 | Derenzo ............................. 250/363.02 |
| 4,879,464 | 11/1989 | Iinuma ......................... 250/363.02 X |
| 4,996,413 | 2/1991 | McDaniel et al. ............. 250/370.11 X |
| 4,999,500 | 3/1991 | Breskin et al. ................. 250/363.02 X |
| 5,118,948 | 6/1992 | Ito et al. ......................... 250/363.02 X |
| 5,171,998 | 12/1992 | Engdahl et al. . |
| 5,218,208 | 6/1993 | Augier et al. . |
| 5,276,615 | 1/1994 | Tournier Edmond et al. . |
| 5,308,986 | 5/1994 | Walker ............................... 250/370.11 |
| 5,347,455 | 9/1994 | Ichihara ........................ 250/363.02 X |

*Primary Examiner*—Carolyn E. Fields
*Assistant Examiner*—Edward J. Glick
*Attorney, Agent, or Firm*—Bobby D. Scearce; Thomas L. Kundert

[57] ABSTRACT

A gamma ray imaging camera system and method for using it are described which in representative embodiments include a gamma ray collimator, a scintillator adjacent the collimator for converting gamma photons into visible photons, a low level visible photon detector including at least two optically coupled inverter tubes, a high-speed lens for imaging the visible photons onto the detector, a video imager for receiving, recording and storing sequential images of the visible photons defining the detector output, and a programmed computer for processing the images and determining the spatial distribution of the images.

16 Claims, 2 Drawing Sheets

GAMMA RAY CAMERA METHOD AND APPARATUS

RIGHTS OF THE GOVERNMENT

The invention described herein may be manufactured and used by or for the Government of the United States for all governmental purposes without the payment of any royalty.

BACKGROUND OF THE INVENTION

The present invention relates generally to gamma ray imaging detectors and more particularly to a gamma ray camera having application in the field of nuclear medicine for providing spatial images of radioactive substances administered into the body to elucidate internal organ functions.

In nuclear medicine practice, gamma emitting radioisotope containing substances may be introduced into an area of the body under examination, such as the thyroid, and may be localized preferentially into a well defined distribution depending on the chemical and biological activity of the substance. Gamma rays are emitted isotropically from the substance at energies characteristic of the isotope. For example, technicium (99 m) generates gamma rays at about 140 Key and, because of its relatively short half-life (<1 day), is used in many nuclear medicine applications. Because radiation from the substance is isotropic, the gamma rays must be collimated in order to obtain an image of the region of the body into which the radioisotope is introduced.

Detecting gamma ray photons in general requires a high gain process to convert a single photon impact into many free electrons that in turn register an electrical impulse in a counter. For this purpose, Anger (U.S. Pat. Nos. 2,776,377; 2,779,876) used scintillation properties of certain crystals and the high gain provided by photomultiplier tubes; the collimator is coupled to a scintillator crystal through a light tight thin barrier that passes gamma photons but blocks visible photons. The scintillation crystal (typically sodium iodide (NaI)) converts a gamma photon (having energies generally greater than about 40 KeV) into a number of visible photons (wavelengths of about 200–1000 nm) proportional to the gamma photon energy. The location of scintillation points is detected by the photomultiplier tube array coupled to the crystal through the light pipe. The whole system is configured in a hexagonal close packed arrangement such that the signal from a given scintillation event excites responses in at least seven photomultiplier tubes, i.e. a central tube and at least the six nearest tubes. Anger combined the magnitude of the signal from each photomultiplier tube to provide a two dimensional position signal indicative of the point of gamma ray absorption. This process required a large electronic system to compute all the coincidental responses from a large set of combinations of typically 72 elements taken 7 at a time.

Proposed improvements in recent years for overcoming the limitations of the Anger camera. have included use of intensifier tubes, position sensing photomultiplier tubes, and arrays of solid state photodetectors, all with very limited success. The intensifier tube proposals have limited sensitivity and resolution because of insufficient gain and high background noise. An example of this type of camera is one proposed by Lo I. Yin (1979), in which the converting scintillation crystal is coupled directly to a fiberoptic faceplate which is coupled to an image intensifier tube. This camera is limited by insufficient gain in the photodetector to cover a large area, and the photodetector must be scaled up to the size of the input crystal to achieve efficient light coupling. More recently, Dilmanian et al (IEEE transactions on Nuclear Science, 37 (1990)) described a gamma imaging system comprising an NaI crystal coupled by a fiberoptic taper to the entrance port of a Hamamatsu microchannel-plate imager (PIAS) photon counting imaging system. Although the imaging system demonstrated an autoradiograpic resolution of about 0.7 mm FWHM, it was limited in cross-sectional dimension to 26 mm. To scale this instrument up to Anger camera dimensions would be prohibitively expensive since conventional imagers have an active diameter of only 15 mm. A factor affecting the Dilmanian et al and similar imagers is that there is no pulse height selection on the detected gamma photon distribution events. This will result in degraded imaging of deep tissue due to Compton scattering, which confounds the gamma isotope distribution image.

An example solid state detector array type of gamma imager by Engdahl et al (U.S. Pat. No. 5,171,998) includes the usual front end gamma scintillator followed by an array of solid state photo-diode detectors, preferably low capacitance silicon drift elements. The impact of the gamma ray photon is tracked in two dimensions by a complex timing scheme on two coordinates. Although small arrays and imaging devices show some promise, limitations arise when making these arrays much larger. Because the photodiodes as described by Engdahl et al are to be directly mounted to the scintillator crystal or light pipe attached to it, there is the possibility of gamma ray photons striking directly on the photodiodes. This could have the effect of creating an intense background event structure which would be difficult to compensate.

Two limitations of the original Anger camera addressed by recent inventions include the inability of the Anger camera to distinguish pulse height and use of NaI as the scintillator. The first limitation does not permit the camera to reject multiple scatter gamma photons which confounds the isotope distribution image. The second is the use of NaI crystal for its blue spectrum center of its scintillation photons. This blue spectrum center was selected for optimum use of photomultiplier tubes which are more sensitive in the blue, although the visible photon yield is notably lower than that of other scintillator crystals. Also, NaI is fragile and hydroscopic, requiring careful handling.

The present invention solves or substantially reduces in critical importance problems with prior art camera structures by providing an inexpensive gamma camera which uses any of several well known gamma scintillation detector crystals such as thallium doped NaI or thallium doped cesium iodide (CsI). The increased photon yield of CsI(Tl), although further into the red spectrum, is a desirable attribute, and CsI is less fragile and easier to handle than NaI and is not hydroscopic. The invention further utilizes a novel high gain, low noise, high quantum efficiency intensifier system combined with a video signal processor to produce images of radioisotope distributions in the body.

It is therefore a principal object of the invention to provide an improved gamma imaging camera system.

It is a further object of the invention to provide a gamma imaging camera utilizing a scintillation crystal that permits retrofit to existing camera systems.

It is a further object of the invention to provide a gamma imaging camera system permitting use of CsI(Tl) as the scintillator crystal which is less fragile, less hydroscopic and has greater photon yield than NaI(Tl).

It is a further object of the invention to provide an economical and portable gamma camera having no light pipes for coupling the scintillator crystals and the photon detector.

It is another object of the invention to provide a gamma imaging camera incorporating a high efficiency coupling lens to capture the scintillation photons from a large area crystal and couple the signal to a small aperture sensor system.

It is a further object of the invention to utilize night vision inverter tube assemblies coupled and operated in a novel manner.

It is another object of the invention to provide a gamma camera having ultra low level detection capability with a gain of about $10^9$ with noise less than $10^{-3}$/pixel/sec.

It is another object of the invention to provide a gamma imaging camera wherein the image processing is simplified by using conventional video camera output with a VCR and personal computer control.

It is a further object of the invention to provide a gamma imaging camera incorporating Compton scatter rejection in the gamma image by thresholding in the image processing.

It is another object of the invention to provide a gamma imaging camera incorporating cosmic ray background rejection by band limiting of the scintillation events in the image processing.

It is yet another object of the invention to provide an ultra-low level (essentially single-photon) visible spectrum imaging camera system.

These and other objects of the invention will become apparent as a detailed description of representative embodiments thereof proceeds.

SUMMARY OF THE INVENTION

In accordance with the foregoing principles and objects of the invention, a gamma ray imaging camera system and method for using it are described which in representative embodiments comprise a gamma my collimator, a scintillator adjacent the collimator for converting gamma photons into visible photons, a low level visible photon detector including at least two optically coupled inverter tubes, a high-speed lens for imaging the visible photons onto the detector, a video imager for receiving, recording and storing sequential images of the visible photons defining the detector output, and a programmed computer for processing the images and determining the spatial distribution of the images.

BRIEF DESCRIPTION OF THE DRAWINGS

The invention will be more fully understood from the following detailed description of representative embodiments thereof read in conjunction with the accompanying drawings wherein.

DETAILED DESCRIPTION

Figure 1:
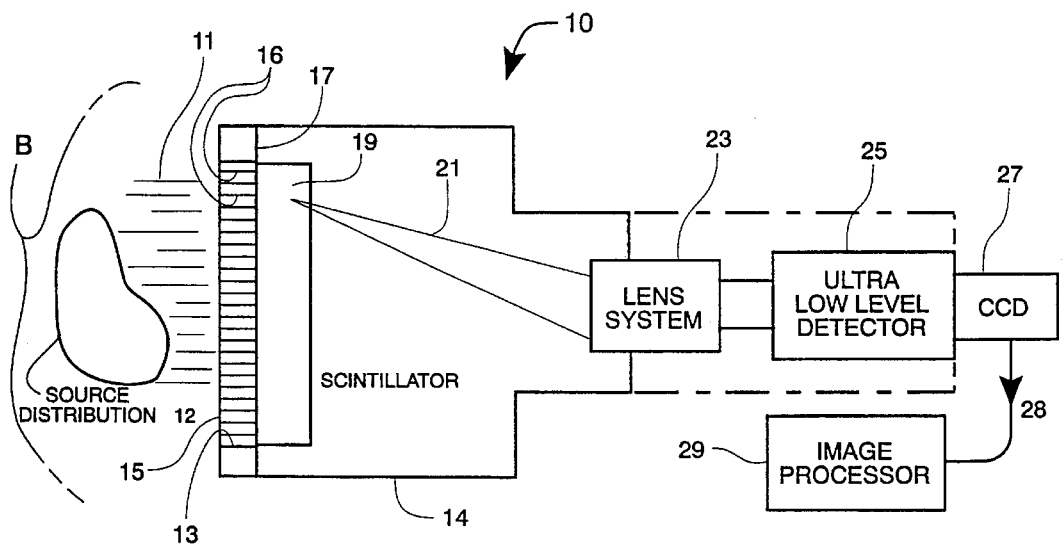
FIG. 1 is a schematic of the component parts of the gamma camera system of the invention.

Referring now to the drawings, FIG. 1 shows a schematic layout of the component parts of representative gamma camera system 10 of the invention. System 10 may be configured for imaging radioisotope distributions in the human body. Gamma radiation (rays) 11, such as from an isotope source distribution 12 within body B, may be directed onto system 10 as at entrance aperture 13 defined in light tight enclosure 14. Collimator 15 is disposed at aperture 13 and comprises a high-Z material such as lead with an array of apertures 16 disposed perpendicularly to the plane of aperture 13. It may be noted at the outset that in some gamma imaging applications, collimating the gamma rays may not be necessary. Accordingly, in one basic embodiment of the invention contemplated herein, gamma collimation means may be omitted. A gamma transparent visible light barrier 17 and scintillation crystal 19 are disposed adjacent collimator 15. Scintillation crystal 19 converts gamma photons by the photoelectric effect into visible photons 21 of longer wavelength detectable by visible light photodetector devices. Scintillation crystal 19 may comprise any well known material conventionally used for this purpose, such as NaI(Tl), CsI(Tl), $CeF_3$, $BaF_2$, ZnS, ZnCdS(Ag) or other phosphors, xenon or other noble gas in gas or liquid form, or bismuth germinate, or crystal 19 may be a polycrystalline layer of scintillator material such as gadolinium oxysulfide activated with terbium or yttrium oxysulfide if low energy x-ray imaging is desired. However, CsI(Tl) may be preferred for gamma imaging because of a characteristic high visible photon yield per incident gamma. A high efficiency short focal length lens system 23 couples the signal defined by photons 21 to a novel ultra high gain, low noise imaging system (detector) 25. Because of the typical large (about 30 cm) diameter of crystal 19, the signal must propagate a distance of about 30 to 40 cm to lens system 23 in order to suitably demagnify the image dimension of source distribution 12. This ratio is about 12:1 for a typical (305 mm diam) crystal used in nuclear medicine and the entrance port (25 mm diam) of a second or third generation night vision device. The aperture of lens system 23 must be large because the yield is only about 5,000 visible photons for the typical nuclear gamma photon (100 to 300 Key). If lens 23 has an aperture of 10 cm, this converts to a fractional interception at 34 cm spacing of $(10/34)^2$, i.e. less than about 10% of the event photon set intercepted. At a quantum efficiency of about 10%, the number of photons involved in production of the image per gamma event is about 40, although other factors might reduce this to about 10 to 20 detected visible photons per gamma photon. Lens system 23 and imaging system 25 must therefore have an extremely high gain with extremely low noise in order to render an image of the process. Video imaging device 27 (such as a vidicon or CCD device) transmits signal 28 to image processing system 29.

Figure 2:
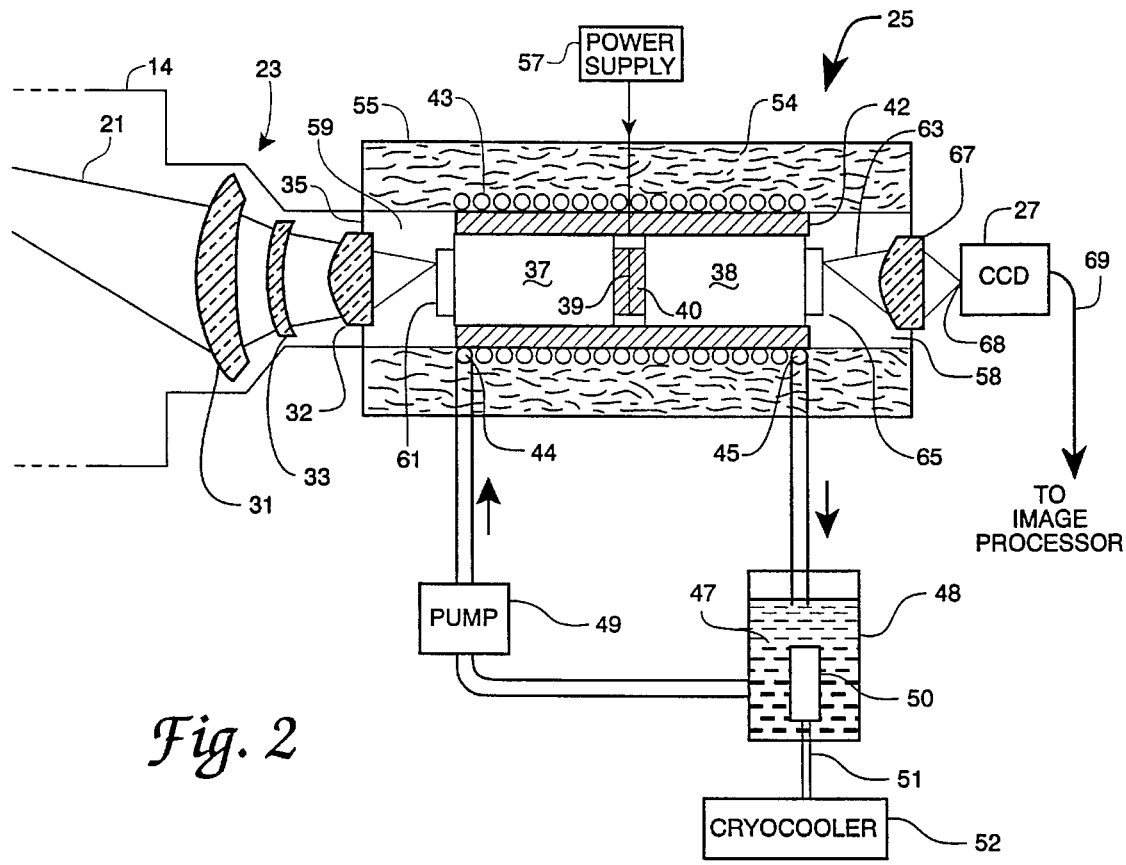
FIG. 2 is a view in axial section of the lens system and low level imaging system of the FIG. 1 camera system.

FIG. 2 shows a detailed axial sectional view of lens system 23 and imaging system 24. In a preferred embodiment suggested in the figures, lens system 23 comprises a three element anti-reflective coated system of two aspheric lenses 31,32 and one miniscus lens 33. Aspheric lens 32 is 50 mm diameter with 40 mm focal length (e.g., Spindler Hoyer catalog #031746). Lens 33 is 80 mm diameter by 200 mm focal length spaced about 2 cm from lens 32. Lens 31 may be the front 100 mm diameter aspheric element of a TV projection lens (e.g., US Precision lens Delta 101A), and is postioned about 3 cm from lens 33. Lens system 23 functions most effectively for visible photons in the 300–900 nm range, and at an f number less than 1.0 and may be replaced by other lens systems as would occur to one skilled in the applicable art guided by these teachings.

Lens system 23 is coupled at light tight seal 35 to imaging system 25. The function of system 25 is to detect with high quantum efficiency and amplify light images with an amplification factor of about $10^9$, but also to maintain the noise level to less than about $10^{-3}$ events/sec/pixel. In the FIG. 2 embodiment, system 25 comprises two commercially available night-vision inverter tubes 37,38 (e.g., Varo AN/PUS-4 IIIGen tube 37; Varo 3603-1 IIGen tube 38) coupled output to input at interface 39 between tubes 37,38 with a low temperature fluid 40 such as ethylene glycol. The IIIGen tube 37 has a gallium arsenide photocathode with very high quantum efficiency into the red (~900 nm), and is very effective with a wide range of scintillators, including CsI which emits red shifted visible photons for a gamma photon photoelectric event. A IIGen tube can be used in 37 if the scintillator is NaI(Tl) which emits predominately in the blue-green spectral region. The output of tube 37 is a fiber optic face plate coupled to the input of tube 38 which also has a fiber optic type window. This arrangement can be coupled and cooled to less than −20° C., including internal high voltage power supplies of the inverter tubes packaged with the tubes. The tubes are cooled by inserting the coupled tube assembly into heat conducting aluminum or copper cylinder 42 wrapped by a copper tube coil 43 having inlet/outlet 44/45 for conducting cooling fluid 47 (such as alcohol) from thermally insulated reservoir 48 using pump 49. Cylinder 42 reduces electrical noise that would otherwise enter the system and uniformly cools tubes 37,38. Fluid 47 temperature is reduced to about −20° C. by cryocooler element 50 in reservoir 48 transporting the cooling process over conduit 51 from cryocooler 52 (e.g., Neslab model CC100F). Other well known methods for low temperature cooling of detectors may be used, such as liquid nitrogen or Peltier effect devices, but the system shown in FIG. 2 may have much less vibrational noise than typical fan cooled Peltier devices and is simpler to handle than liquid nitrogen.

The cooled detector assembly is surrounded by thermal insulation material 54 (such as STYROFOAM) and light tight metal enclosure 55. The inverter tubes are powered by an external low voltage power supply 57. Region 59 between lens system 23 and entrance port 61 of imaging system is filled with inert gas such as nitrogen to insulate lens 32 (at room temperature) from the cooled detector 25 assembly. Conversely, region 59 may be evacuated. Photons 21 are projected by lens system 23 onto the entrance port 61 of first inverter tube 37. The inverter tubes amplify the input light signal by photoelectron emission, acceleration, focusing and micro channel plate amplification. Because tube 37 has a gallium arsenide photocathode, system 25 has a very high quantum efficiency for red spectrum generating scintillation crystals such as CsI(Tl). These tubes provide a gain of about 30,000 each and, when coupled as shown, yield a gain of $30,000^2$ or about $10^9$ as desired. The spontaneous thermal emission of all surfaces is drastically reduced when the system is cooled to less than −20° C.

The resultant amplified light signal 63 at output stage 65 of tube 38 is coupled by lens 67 onto a point 68 on CCD device 27. Lens 67 also seals region 58 filled with inert gas such as nitrogen to insulate the lens from the cooled interior. Lens 67 is a close up lens that falls the field of device 27. Output signal 69 of device 27 containing the positional and intensity information of the scintillation event is fed into image processing system 29 (FIG. 1).

Figure 3:
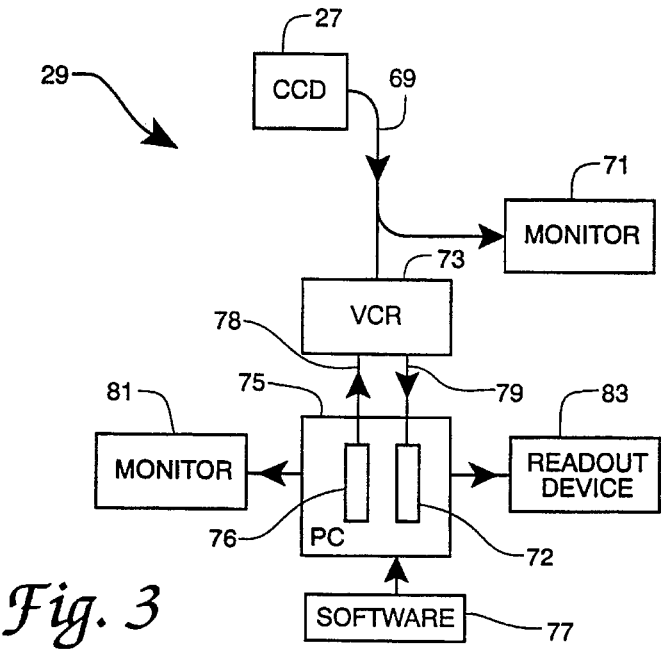
FIG. 3 is a schematic block diagram of the essential components of the imaging device of the FIG 1 camera system.

Referring now to FIG. 3, shown therein is a schematic block diagram of the essential components of imaging processer 29. Signal 69 from device 27 is first displayed on a real-time monitor 71. The image comprises small star-like bursts indicating a gamma interaction or wide area bursts indicating typical cosmic ray background events. Signal 69 is also fed to a conventional video cassette recorder (VCR) 73 which is controlled in operation by computer (PC) 75 controlled from software storage unit 77. The recorded video signal 79 is transmitted to a typical video image frame data acquisition plug-in board 72 (such as an Imaging Technology Vision Plus-AT OFG) within PC 75. The computer program controls the data acquisition at VCR 73 by means of a computer I/O board 76 over control lines 78, rendering the desired outputs at monitor 81 or readout device 83.

Figure 4:
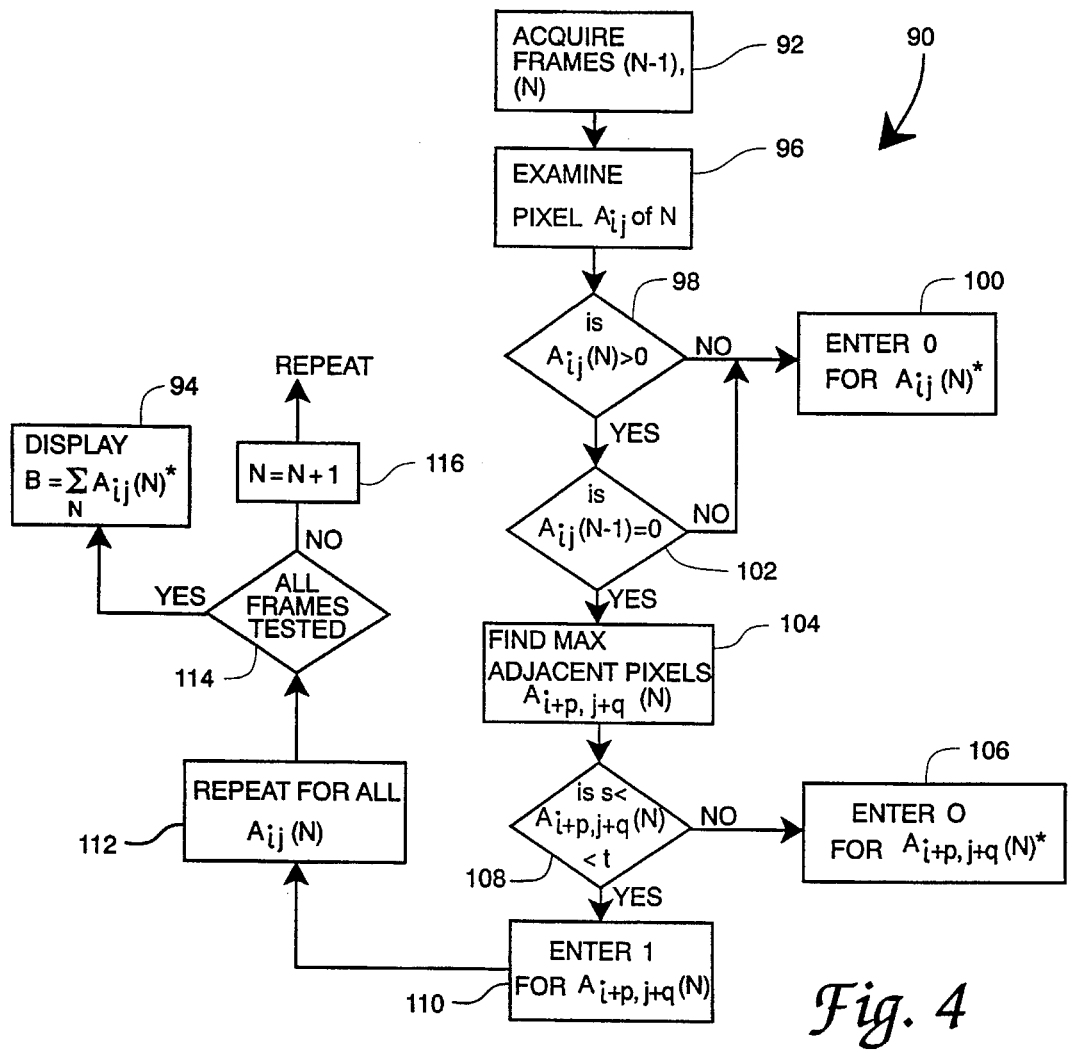
FIG. 4 is a flow diagram of the operational control process for the FIG. 1 camera system.

Referring now to FIG. 4, shown therein is a flow diagram of operational control process 90 for camera system 10. Computer 75 starts and stops the video taping of the gamma imaging process, collects a thorough record of scintillation events produced by imaging system 27, and then analyzes the images frame-by-frame. For each frame N in a sequence, computer 75 digitizes and stores a digital record of frame N and N−1 (FIG. 4, block 92). In the step labeled 96, each pixel of frames N and N−1 is examined for the analog-to-digital conversion value. If the element $A_{ij}(N)$ is zero, zero is entered in a composite image $A_{ij}(N)^*$ of the Nth frame (block 100). If $A_{ij}(N)$ is non-zero, the program tests to see (block 102) if the $A_{ij}(N-1)$ at frame N−1 is zero. If the $A_{ij}$ element at the previous frame is not zero, then the $A_{ij}(N)^*$ pixel of the composite frame is set to zero. This is done to eliminate an after image event from being registered multiple times in the composite frame. If, however, the $A_{ij}(N-1)$ of the previous frame is zero (block 102) then computer 75 searches (block 104) for non-zero pixels $A_{i+p,j+q}(N)$ adjacent to $A_{ij}(N)$ and to determine which of these are maximum. This is done to find the local maximum pixel representing the scintillation event. The magnitude of the pixels obtained (block 104) is compared (block 108) to a range s<x<t. The lower limit s and the upper limit t are preprogrammed into software storage unit 77. The purpose of this selection process is to cancel scintillation events that are too low due to multiple scatter by a Compton process or too high and caused by a cosmic ray event. If the maximum pixel(s) do not satisfy this window criteria, zeros are entered in composite frame $A_{i+p,j+q}(N)^*$ (block 106) or if the criterion is satisfied, a value of 1 is entered in the composite frame (block 110). The process is repeated for all pixels for a given frame (block 112) and composite frames are generated for each frame of the run under analysis (blocks 114,116). Once all frames are tested, the program computes a super composite frame $B=A_{ij}(N)^*$ (block 94). The resultant high quality image of the isotope distribution is then displayed (block 94). Obtaining images of a time cycled process such as a beating heart can be greatly facilitated by this system by putting a time marker on the video recording synchronized with the process. Computer 75 is then directed to examine only those frames in a particular point in the cycle relative to the time marker and compose images with that subset of frames.

The invention therefore provides an improved gamma camera system having particular utility in the field of nuclear medicine. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:

1. A gamma ray imaging camera system comprising:
   (a) gamma ray collimating means;
   (b) scintillation means adjacent said collimating means for converting gamma photons into visible photons;
   (c) visible photon detection means including at least two optically coupled inverter tubes and means for cooling said inverter tubes;
   (d) a lens for imaging said visible photons onto said detection means;
   (e) video imaging means for receiving, recording and storing sequential images of said visible photons defining the output of said detection means; and
   (f) means for determining the spatial distribution of said images of said visible photons.

2. The system of claim 1 wherein said means for determining the spatial distribution of said images includes a programmed computer for processing said images from said video imaging means and for interpreting the spatial distribution of said images.

3. The system of claim 1 wherein said scintillation means includes a scintillator material selected from the group consisting of thallium activated sodium iodide, thallium activated cesium iodide, cerium fluoride, barium fluoride, zinc sulfide, zinc cadmium sulfide, bismuth germanate, terbium activated gadolinium oxysulfide, yttrium oxysulfide, and the noble gases.

4. The system of claim 1 wherein said lens is a multiple element aspheric type.

5. A gamma ray imaging camera system comprising:
   (a) scintillation means for converting gamma photons into visible photons;
   (b) visible photon detection means including at least two optically coupled inverter tubes and means for cooling said inverter tubes;
   (c) a lens for imaging said visible photons onto said detection means; and
   (d) video imaging means for receiving, recording and storing sequential images of said visible photons defining the output of said detection means.

6. The system of claim 5 further comprising gamma ray collimating means adjacent said scintillation means.

7. The system of claim 5 further comprising means for determining the spatial distribution of said images including a programmed computer for processing said images from said video imaging means and for interpreting the spatial distribution of said images.

8. The system of claim 5 wherein said scintillation means includes a scintillator material selected from the group consisting of thallium activated sodium iodide, thallium activated cesium iodide, cerium fluoride, barium fluoride, zinc sulfide, zinc cadmium sulfide, bismuth germanate, terbium activated gadolinium oxysulfide, yttrium oxysulfide, and the noble gases.

9. The system of claim 5 wherein said lens is a multiple element aspheric type.

10. An ultralow light level imaging camera system, comprising:
    (a) a camera lens;
    (b) visible photon detection means including at least two optically coupled inverter tubes and means for cooling said inverter tubes; and
    (c) video imaging means for receiving, recording and storing sequential images of said visible photons defining the output of said detection means.

11. The system of claim 10 wherein said camera lens is a multiple aspheric type.

12. The system of claim 9 further comprising means for determining the spatial distribution of said images including a programmed computer for processing said images from said video imaging means and for interpreting the spatial distribution of said images.

13. A method for gamma ray imaging comprising the steps of:
    (a) providing a source of gamma rays;
    (b) converting gamma photons from said source into visible photons;
    (c) detecting and amplifying said visible photons using at least two cooled optically coupled inverter tubes;
    (d) optically imaging said visible photons onto said coupled inverter tubes for providing sequential amplified images of said visible photons;
    (e) storing said sequential amplified images of said visible photons; and
    (f) determining the spatial distribution of said sequential amplified images of said visible photons.

14. The method of claim 13 wherein said step of determining the spatial distribution of said amplified images is performed using a programmed computer for processing said amplified images and for interpreting the spatial distribution of said amplified images.

15. The method of claim 13 wherein the step of converting gamma photons into visible photons is performed using scintillation means.

16. The method of claim 15 wherein said scintillation means includes a scintillator material selected from the group consisting of thallium activated sodium iodide, thallium activated cesium iodide, cerium fluoride, barium fluoride, zinc sulfide, zinc cadmium sulfide, bismuth germanate, terbium activated gadolinium oxysulfide, yttrium oxysulfide, and the noble gases.

* * * * *

UNITED STATES PATENT AND TRADEMARK OFFICE
CERTIFICATE OF CORRECTION

PATENT NO. : 5,521,386

DATED: : May 28, 1996

INVENTOR(S) : John Taboada

It is certified that error appears in the above-identified patent and that said Letters Patent is hereby corrected as shown below:

Column 1, line 25, "Key" should read --- Kev ---.
Column 3, line 41, "my" should read --- ray ---.
Column 4, line 43, "Key" should read --- Kev ---.
Column 5, line 3, "fight" should read --- tight ---.
Column 5, line 62, "falls" should read --- fills ---.
Column 8, line 17, "9" should read --- 10 ---.

Signed and Sealed this

Thirty-first Day of December, 1996

Attest:

BRUCE LEHMAN

Attesting Officer

Commissioner of Patents and Trademarks